United States Patent
Shelton, IV et al.

(10) Patent No.: US 7,380,696 B2
(45) Date of Patent: Jun. 3, 2008

(54) ARTICULATING SURGICAL STAPLING INSTRUMENT INCORPORATING A TWO-PIECE E-BEAM FIRING MECHANISM

(75) Inventors: Frederick E. Shelton, IV, Hillsboro, OH (US); Kevin Ross Doll, Mason, OH (US); Jerry R. Morgan, Cincinnati, OH (US); Michael Earl Setser, Burlington, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 105 days.

(21) Appl. No.: 10/955,042

(22) Filed: Sep. 30, 2004

(65) Prior Publication Data

US 2005/0263562 A1  Dec. 1, 2005

Related U.S. Application Data

(63) Continuation-in-part of application No. 10/443,617, filed on May 20, 2003, now Pat. No. 6,978,921.

(60) Provisional application No. 60/591,694, filed on Jul. 28, 2004.

(51) Int. Cl.
*A61B 17/68* (2006.01)
(52) U.S. Cl. .............. 227/175.1; 227/176.1; 227/178.1; 227/19
(58) Field of Classification Search ........... 227/175.2, 227/175.1, 176.1, 178.1, 180.1
See application file for complete search history.

(56) References Cited

U.S. PATENT DOCUMENTS

| | | | |
|---|---|---|---|
| 4,429,695 A | 2/1984 | Green | |
| 5,031,814 A | 7/1991 | Tompkins et al. | |
| 5,071,052 A | 12/1991 | Rodak et al. | |
| 5,137,198 A | 8/1992 | Nobis et al. | |
| 5,312,023 A | 5/1994 | Green et al. | |
| 5,397,046 A | 3/1995 | Savage et al. | |
| 5,413,267 A | 5/1995 | Solyntjes et al. | |
| 5,413,268 A | 5/1995 | Green et al. | |
| 5,445,304 A | 8/1995 | Plyley et al. | |
| 5,465,895 A | 11/1995 | Knodel et al. | |
| 5,484,095 A | 1/1996 | Green et al. | |
| 5,535,937 A | 7/1996 | Boiarski et al. | |
| 5,584,425 A | 12/1996 | Savage et al. | |
| 5,624,452 A | 4/1997 | Yates | |
| 5,634,584 A * | 6/1997 | Okorocha et al. | ........ 227/176.1 |
| 5,673,840 A | 10/1997 | Schulze et al. | |
| 5,680,983 A | 10/1997 | Plyley et al. | |
| 5,692,668 A | 12/1997 | Schulze et al. | |
| 5,709,334 A | 1/1998 | Sorrentino et al. | |

(Continued)

*Primary Examiner*—Rinaldi I. Rada
*Assistant Examiner*—Michelle Lopez
(74) *Attorney, Agent, or Firm*—Frost Brown Todd. LLC

(57) ABSTRACT

A surgical severing and stapling instrument, suitable for laparoscopic and endoscopic clinical procedures, clamps tissue within an end effector of an elongate channel pivotally opposed by an anvil. An E-beam firing bar moves distally through the clamped end effector to sever tissue and to drive staples on each side of the cut. The E-beam firing bar affirmatively spaces the anvil from the elongate channel to assure properly formed closed staples, especially when an amount of tissue is clamped that is inadequate to space the end effector. In particular, an upper pin of the firing bar longitudinally moves through an anvil slot and a channel slot is captured between a lower cap and a middle pin of the firing bar to assure a minimum spacing. Forming the E-beam from a thickened distal portion and a thinned proximal strip enhances manufacturability and facilitates use in such articulating surgical instruments.

16 Claims, 15 Drawing Sheets

U.S. PATENT DOCUMENTS

| | | |
|---|---|---|
| 5,735,445 A | 4/1998 | Vidal et al. |
| 5,797,537 A | 8/1998 | Oberlin et al. |
| 5,865,361 A | 2/1999 | Milliman et al. |
| 5,918,791 A | 7/1999 | Sorrentino et al. |
| 6,010,054 A | 1/2000 | Johnson et al. |
| 6,032,849 A | 3/2000 | Mastri et al. |
| 6,079,606 A | 6/2000 | Milliman et al. |
| 6,109,500 A | 8/2000 | Alli et al. |
| 6,330,965 B1 * | 12/2001 | Milliman et al. ......... 227/176.1 |
| 6,669,073 B2 * | 12/2003 | Milliman et al. ......... 227/175.2 |
| 6,786,382 B1 | 9/2004 | Hoffman |
| 6,830,174 B2 * | 12/2004 | Hillstead et al. ......... 227/175.1 |
| 6,964,363 B2 * | 11/2005 | Wales et al. ............. 227/175.1 |
| 6,978,921 B2 * | 12/2005 | Shelton et al. ........... 227/176.1 |
| 6,981,628 B2 * | 1/2006 | Wales ....................... 227/178.1 |
| 6,988,649 B2 * | 1/2006 | Shelton et al. ........... 227/175.2 |
| 7,055,731 B2 * | 6/2006 | Shelton, IV et al. ..... 227/176.1 |
| 7,111,769 B2 * | 9/2006 | Wales et al. ............. 227/178.1 |
| 2001/0029384 A1 | 10/2001 | Nicholas et al. |
| 2001/0030219 A1 | 10/2001 | Green et al. |
| 2002/0117533 A1 | 8/2002 | Milliman et al. |
| 2004/0232196 A1 | 11/2004 | Shelton et al. |
| 2004/0232197 A1 | 11/2004 | Shelton et al. |
| 2005/0006431 A1 * | 1/2005 | Shelton et al. ........... 227/175.1 |
| 2005/0006434 A1 | 1/2005 | Wales et al. |
| 2006/0016853 A1 * | 1/2006 | Racenet .................... 227/176.1 |
| 2006/0025813 A1 * | 2/2006 | Shelton et al. ............. 606/205 |
| 2007/0187453 A1 | 8/2007 | Smith et al. |

* cited by examiner

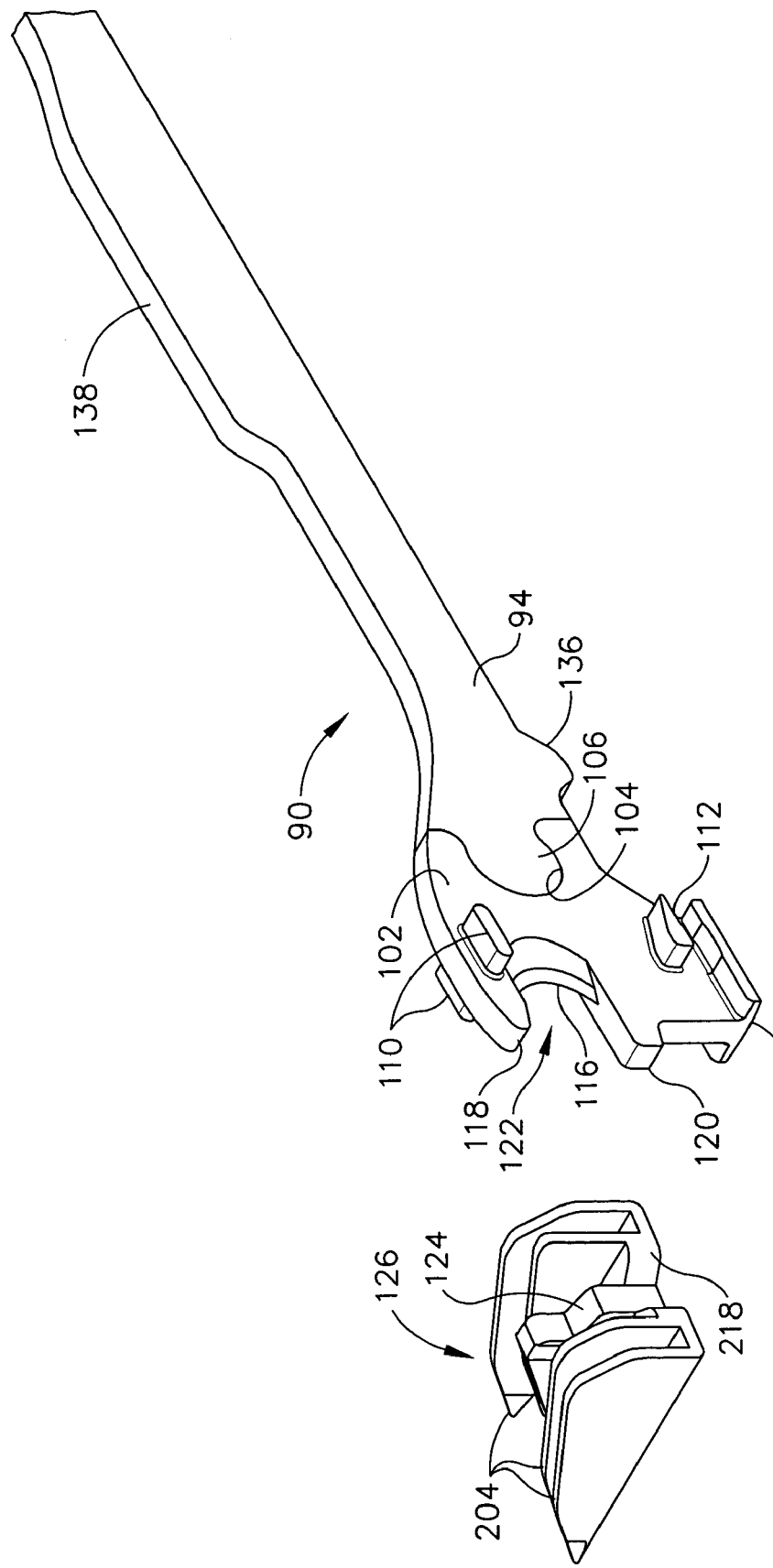

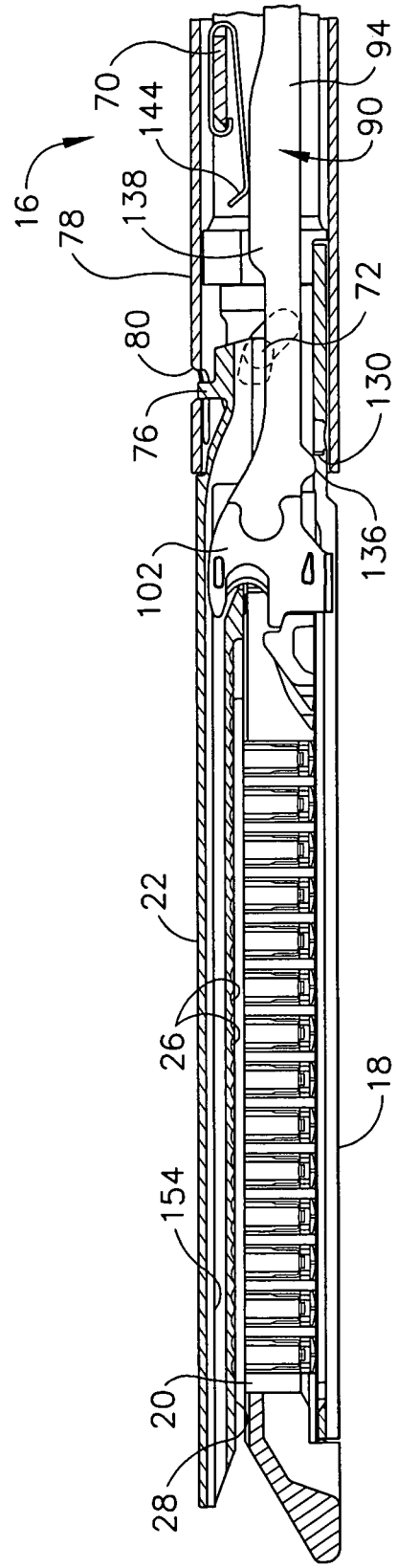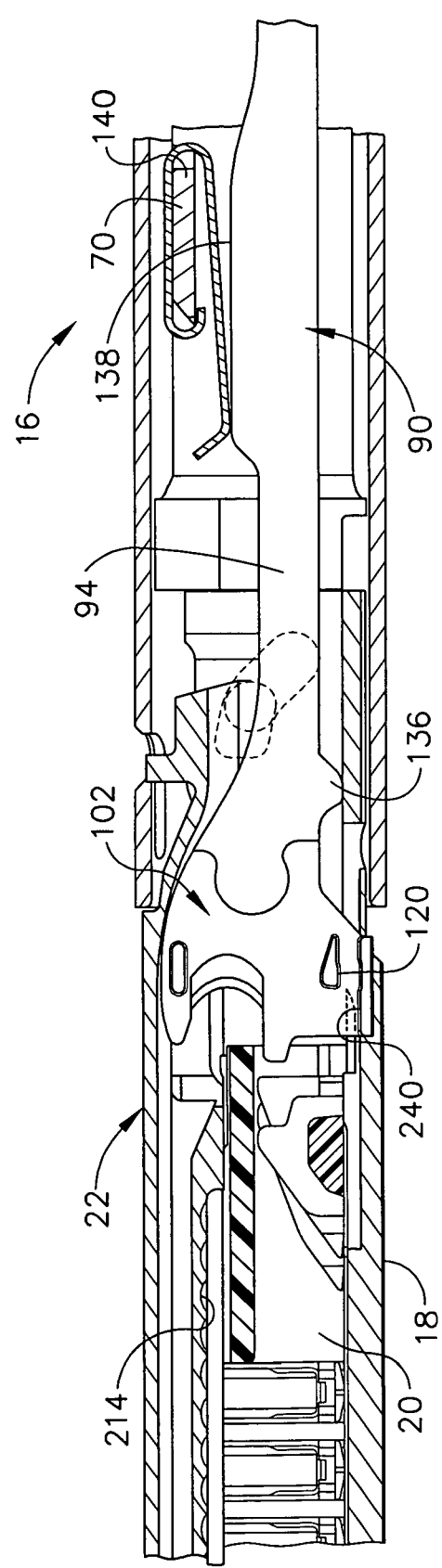

ARTICULATING SURGICAL STAPLING INSTRUMENT INCORPORATING A TWO-PIECE E-BEAM FIRING MECHANISM

The present application hereby claims the benefit of the U.S. provisional patent application entitled "SURGICAL INSTRUMENT INCORPORATING AN ELECTRICALLY ACTUATED ARTICULATION MECHANISM", to Shelton, Ser. No. 60/591,694, filed on 28 Jul. 2004. The present application is a continuation-in-part patent application of the U.S. nonprovisional patent application entitled "SURGICAL STAPLING INSTRUMENT INCORPORATING AN E-BEAM FIRING MECHANISM" to Shelton et al., Ser. No. 10/443,617, filed on 20 May 2003, now U.S. Pat. No. 6,978,921 the disclosure of which is hereby incorporated by reference in its entirety.

FIELD OF THE INVENTION

The present invention relates in general to surgical instruments that are suitable for endoscopically inserting an end effector that is actuated by a longitudinally driven firing member, and more particularly a surgical stapling and severing instrument that has an articulating shaft.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Positioning the end effector is constrained by the trocar. Generally these endoscopic surgical instruments include a long shaft between the end effector and a handle portion manipulated by the clinician. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

More recently, U.S. patent Ser. No. 10/443,617, "SURGICAL STAPLING INSTRUMENT INCORPORATING AN E-BEAM FIRING MECHANISM" to Shelton et al., filed on 20 May 2003, which has been incorporated by reference in its entirety, describes an improved "E-beam" firing bar for severing tissue and actuating staples. Some of the additional advantages include affirmatively spacing the jaws of the end effector, or more specifically a staple applying assembly, even if slightly too much or too little tissue is clamped for optimal staple formation. Moreover, the E-beam firing bar engages the end effector and staple cartridge in a way that enables several beneficial lockouts to be incorporated.

Depending upon the nature of the operation, it may be desirable to further adjust the positioning of the end effector of an endoscopic surgical instrument. In particular, it is often desirable to orient the end effector at an axis transverse to the longitudinal axis of the shaft of the instrument. The transverse movement of the end effector relative to the instrument shaft is conventionally referred to as "articulation". This is typically accomplished by a pivot (or articulation) joint being placed in the extended shaft just proximal to the staple applying assembly. This allows the surgeon to articulate the staple applying assembly remotely to either side for better surgical placement of the staple lines and easier tissue manipulation and orientation. This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation.

In co-pending and commonly owned U.S. patent application Ser. No. 10/615,973, "SURGICAL INSTRUMENT INCORPORATING AN ARTICULATION MECHANISM HAVING ROTATION ABOUT THE LONGITUDINAL AXIS", to Frederick E. Shelton IV et al, the disclosure of which is hereby incorporated by reference in its entirety, a rotational motion is used to transfer articulation motion as an alternative to a longitudinal motion.

In the application entitled "SURGICAL STAPLING INSTRUMENT INCORPORATING AN E-BEAM FIRING MECHANISM" to Shelton et al., Ser. No. 10/443,617, filed on 20 May 2003, the disclosure of which was previously incorporated by reference in its entirety, a surgical severing and stapling instrument, suitable for laparoscopic and endoscopic clinical procedures, clamps tissue within an end effector of an elongate channel pivotally opposed by an anvil. An E-beam firing bar moves distally through the clamped end effector to sever tissue and to drive staples on each side of the cut. The E-beam firing bar affirmatively spaces the anvil from the elongate channel to assure properly formed closed staples, especially when an amount of tissue is clamped that is inadequate to space the end effector. In particular, an upper pin of the firing bar longitudinally moves through an anvil slot and a channel slot is captured between a lower cap and a middle pin of the firing bar to assure a minimum spacing. While this E-beam firing bar has a number of advantages, additional features are desirable to enhance manufacturability and to minimize dimensional variations.

Consequently, a significant need exists for a surgical instrument with a firing bar that advantageously assures proper spacing between clamped jaws of an end effector and which facilitates articulation of its shaft.

BRIEF SUMMARY OF THE INVENTION

The invention overcomes the above-noted and other deficiencies of the prior art by providing a firing mechanism that affirmatively vertically spaces an end effector of a surgical stapling and severing instrument. Thus, the instrument structurally assures adequate spacing to achieve proper stapling, even in instances where too little tissue is clamped in the end effector. Integrally forming these features into an E-beam that includes a cutting edge realizes consistent spacing and performance as the E-beam fires through an end effector such as a severing and stapling assembly. Further, proximally attaching a separate, thinned firing bar to the E-beam enhances use in articulating surgical instruments wherein reduced cross sectional area and the ability to flex in a plane of articulation are desirable.

In one aspect of the invention, a surgical instrument includes a handle portion operable to produce a firing motion that actuates an implement portion. This implement portion has an elongate channel that receives a staple cartridge opposed by a pivotally attached anvil. A firing device includes a distally presented cutting edge longitudinally received between the elongate channel and the anvil, an upper member engageable to the anvil channel, a lower member engaging the channel slot, and a middle member operable to actuate the wedge sled, which is integral to the staple cartridge. The middle member advantageously opposes pinching of the end effector, assuring proper staple formation even when an otherwise too small amount of tissue has been clamped. These spacing and cutting features are advantageously formed into an E-beam while flexibility for articulation is provided by a thinned firing bar attached to the E-beam.

These and other objects and advantages of the present invention shall be made apparent from the accompanying drawings and the description thereof.

DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4 is a perspective view of a two-piece knife and firing bar ("E-beam") of the staple applying assembly of FIG. 2.

FIG. 5 is a perspective view of a wedge sled of a staple cartridge of the staple applying assembly of FIG. 1.

FIG. 9 is a left side view in elevation taken generally along the longitudinal axis of line 6—6 of a closed staple applying assembly of FIG. 2 to include center contact points between the two-piece knife and wedge sled but also laterally offset to show staples and staple drivers within the staple cartridge.

FIG. 10 is a left side detail view in elevation of the staple applying assembly of FIG. 9 with the two-piece knife retracted slightly more as typical for staple cartridge replacement.

DETAILED DESCRIPTION OF THE INVENTION

Figure 1:
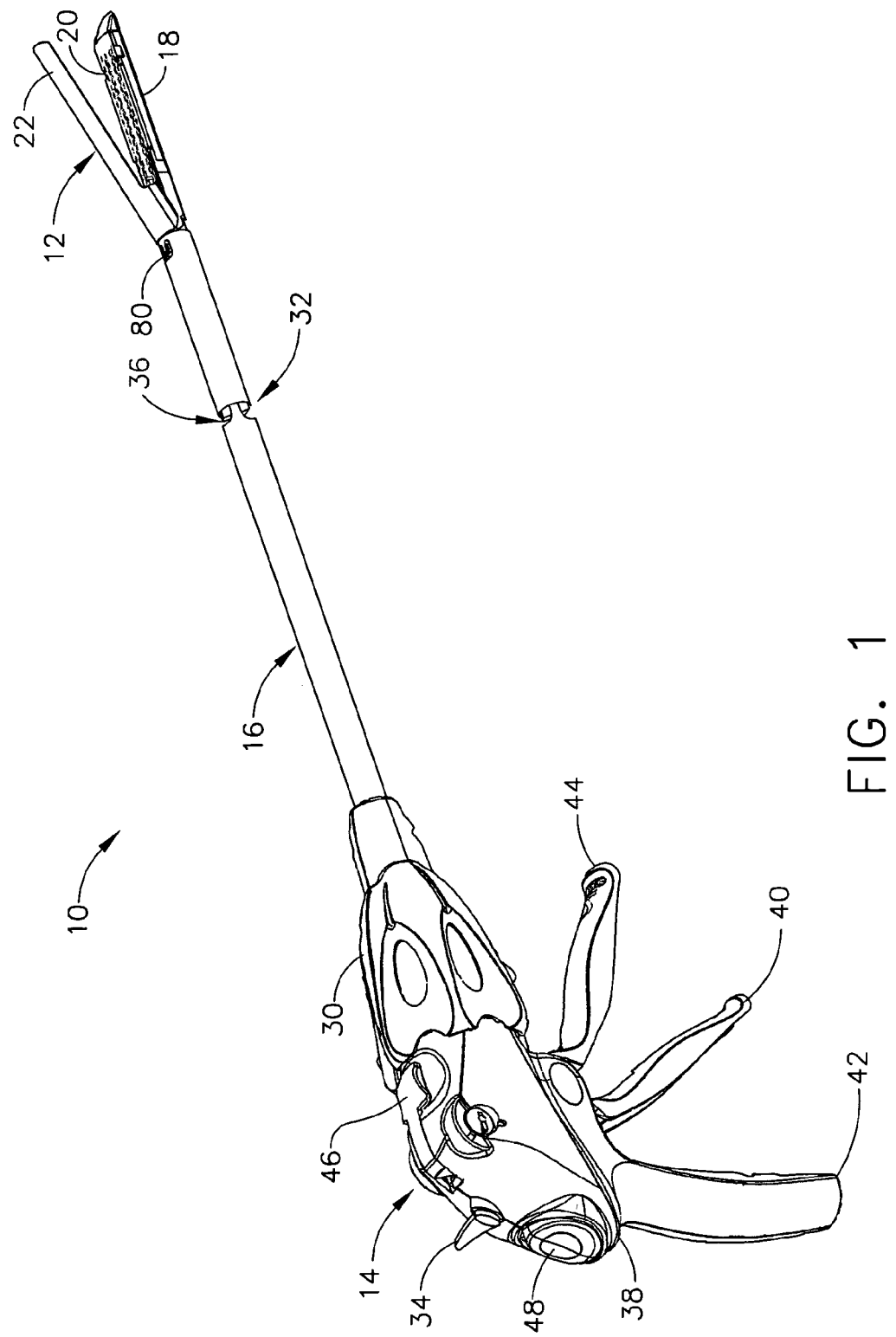
FIG. 1 is a perspective view of an endoscopic surgical stapling instrument for surgical stapling and severing in an open, unarticulated state.
Figure 2:
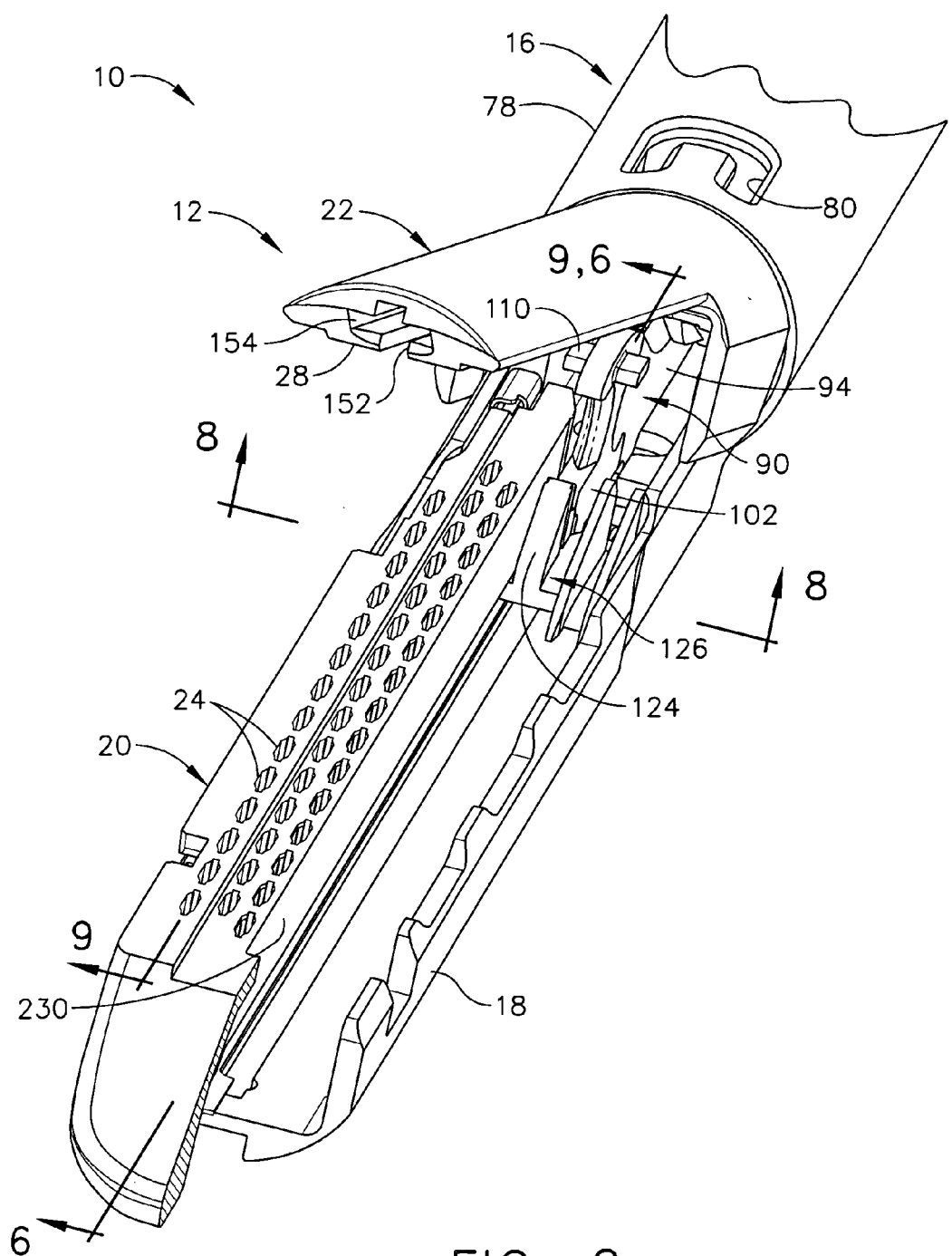
FIG. 2 is a left, front perspective view of an open staple applying assembly of the surgical stapling instrument of FIG. 1 with a right half portion of a replaceable staple cartridge included in a staple channel.
Figure 3:
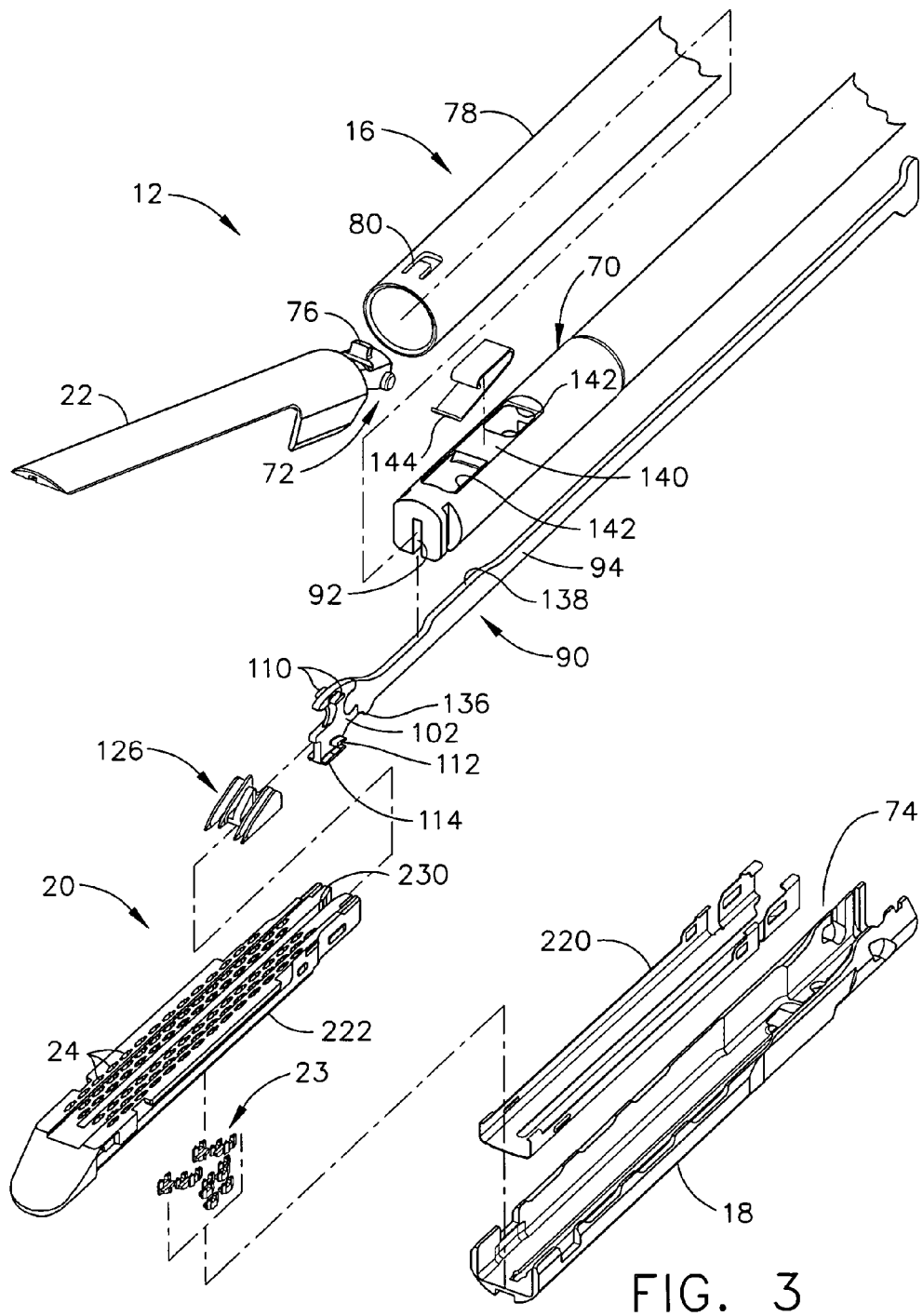
FIG. 3 is an exploded perspective view of the staple applying assembly of FIG. 2 with a complete replaceable staple cartridge and an alternative nonarticulating shaft configuration.

In FIGS. 1–3, a surgical stapling instrument 10 has at its distal end an end effector, depicted as a staple applying assembly 12, spaced apart from a handle 14 (FIG. 2) by an elongate shaft 16. The staple applying assembly 12 includes a staple channel 18 for receiving a replaceable staple cartridge 20. Pivotally attached to the staple channel 18 is an anvil 22 that clamps tissue to the staple cartridge 20 and serves to deform staples 23 (FIG. 3) driven up from staple holes 24 in the staple cartridge 20 against staple forming recesses 26 (FIG. 6) in an anvil undersurface 28 into a closed shape. When the staple applying assembly 12 is closed, its cross sectional area, as well as the elongate shaft 16 are suitable for insertion through a small surgical opening, such as through a cannula of a trocar (not shown).

With particular reference to FIG. 1, correct placement and orientation of the staple applying assembly 12 is facilitated by controls on the handle 14. In particular, a rotation knob 30 causes rotation of the shaft 16 about its longitudinal axis, and hence rotation of the staple applying assembly 12. Additional positioning is enabled at an articulation joint 32 in the shaft 16 that pivots the staple applying assembly 12 in an arc from the longitudinal axis of the shaft 16, thereby allowing placement behind an organ or allowing other instruments such as an endoscope (not shown) to be oriented behind the staple applying assembly 12. This articulation is advantageously effected by an articulation control switch 34 on the handle 14 that transmits an electrical signal to the articulation joint 32 to an Electroactive Polymer (EAP) actuator 36, powered by an EAP controller and power supply 38 contained within the handle 14.

Once positioned with tissue in the staple applying assembly 12, a surgeon closes the anvil 22 by drawing a closure trigger 40 proximally toward a pistol grip 42. Once clamped thus, the surgeon may grasp a more distally presented firing trigger 44, drawing it back to effect firing of the staple applying assembly 12, which in some applications is achieved in one single firing stroke and in other applications by multiple firing strokes. Firing accomplishes simultaneously stapling of at least two rows of staples while severing the tissue therebetween.

Retraction of the firing components may be automatically initiated upon full travel. Alternatively, a retraction lever 46 may be drawn aft to effect retraction. With the firing components retracted, the staple applying assembly 12 may be unclamped and opened by the surgeon slightly drawing the closure trigger 40 aft toward the pistol grip 42 and depressing a closure release button 48 and then releasing the closure trigger 40, thereby releasing the two stapled ends of severed tissue from the staple applying assembly 12.

Staple Applying Assembly.

While an articulation joint 32 is depicted in FIG. 1, for clarity and as an alternative application, the surgical stapling instrument 10 of FIGS. 2–14 omit an articulation joint 32. It should be appreciated, however, that aspects of the present invention have particular advantages for articulation as described below with regard to FIGS. 15–18.

In FIGS. 1–3, the staple applying assembly 12 accomplishes the functions of clamping onto tissue, driving staples and severing tissue by two distinct motions transferred longitudinally down the shaft 16 over a shaft frame 70. This shaft frame 70 is proximally attached to the handle 14 and coupled for rotation with the rotation knob 30. An illustrative multi-stroke handle 14 for the surgical stapling and severing instrument 10 of FIG. 1 is described in greater detail in the co-pending and co-owned U.S. patent application entitled "SURGICAL STAPLING INSTRUMENT INCORPORATING A MULTISTROKE FIRING POSITION INDICATOR AND RETRACTION MECHANISM" to Swayze and Shelton, Ser. No. 10/374,026, the disclosure of which is hereby incorporated by reference in its entirety, with additional features and variation as described herein. While a multi-stroke handle 14 advantageously supports applications with high firing forces over a long distance, applications consistent with the present invention may incorporate a single firing stroke, such as described in co-pending and commonly owned U.S. patent application "SURGICAL STAPLING INSTRUMENT HAVING SEPARATE DISTINCT CLOSING AND FIRING SYSTEMS" to Frederick E. Shelton IV, Michael E. Setser, and Brian J. Hemmelgarn, Ser. No. 10/441,632, the disclosure of which is hereby incorporated by reference in its entirety.

With particular reference to FIG. 3, the distal end of the shaft frame 70 is attached to the staple channel 18. The anvil 22 has a proximal pivoting end 72 that is pivotally received within a proximal end 74 of the staple channel 18, just distal to its engagement to the shaft frame 70. The pivoting end 72 of the anvil 22 includes a closure feature 76 proximate but distal to its pivotal attachment with the staple channel 18. Thus, a closure tube 78, whose distal end includes a horseshoe aperture 80 that engages this closure feature 76, selectively imparts an opening motion to the anvil 22 during proximal longitudinal motion and a closing motion to the anvil 22 during distal longitudinal motion of the closure tube 78 sliding over the shaft frame 70 in response to the closure trigger 40.

The shaft frame 70 encompasses and guides a firing motion from the handle 14 through a longitudinally reciprocating, two-piece knife and firing bar 90. In particular, the shaft frame 70 includes a longitudinal firing bar slot 92 that receives a proximal portion of the two-piece knife and firing bar 90, specifically a laminate tapered firing bar 94. It should be appreciated that the laminated tapered firing bar 94 may be substituted with a solid firing bar or of other materials in applications not intended to pass through an articulation joint, such as depicted in FIGS. 2–14.

An E-beam 102 is the distal portion of the two-piece knife and firing bar 90, which facilitates separate closure and firing as well as spacing of the anvil 22 from the elongate staple channel 18 during firing. With particular reference to FIGS. 3–4, in addition to any attachment treatment such as brazing or an adhesive, the knife and firing bar 90 are formed of a female vertical attachment aperture 104 proximally formed in the E-beam 102 that receives a corresponding male attachment member 106 distally presented by the laminated tapered firing bar 94, allowing each portion to be formed of a selected material and process suitable for their disparate functions (e.g., strength, flexibility, friction). The E-beam 102 may be advantageously formed of a material having suitable material properties for forming a pair of top pins 110, a pair of middle pins 112 and a bottom pin or foot 114, as well as being able to acquire a sharp cutting edge 116. In addition, integrally formed and proximally projecting top guide 118 and middle guide 120 bracketing each vertical end of the cutting edge 116 further define a tissue staging area 122 assisting in guiding tissue to the sharp cutting edge 116 prior to being severed. The middle guide 120 also serves to engage and fire the staple applying apparatus 12 by abutting a stepped central member 124 of a wedge sled 126 (FIG. 5) that effects staple formation by the staple applying assembly 12, as described in greater detail below.

Forming these features (e.g., top pins 110, middle pins 112, and bottom foot 114) integrally with the E-beam 102 facilitates manufacturing at tighter tolerances relative to one another as compared to being assembled from a plurality of parts, ensuring desired operation during firing and/or effective interaction with various lockout features of the staple applying assembly 12.

Figure 6:
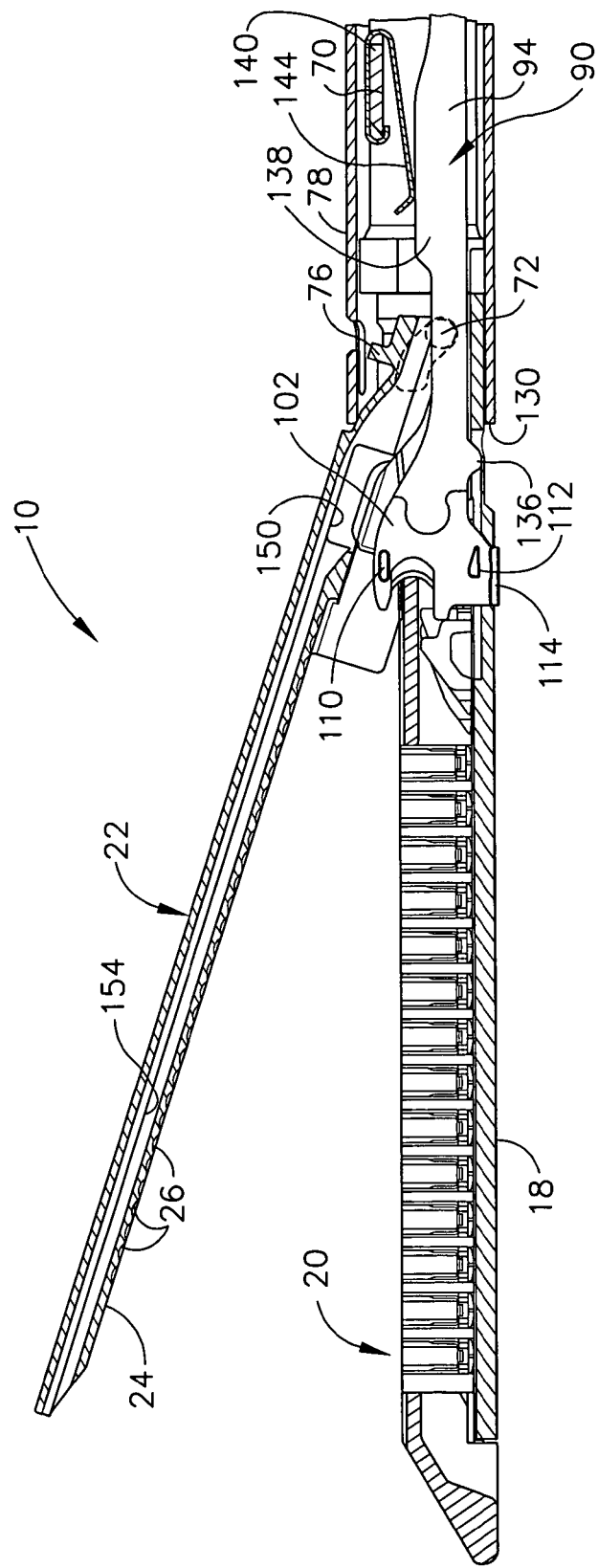
FIG. 6 is a left side view in elevation taken in longitudinal cross section along a centerline line 6—6 of the staple applying assembly of FIG. 2.
Figure 7:
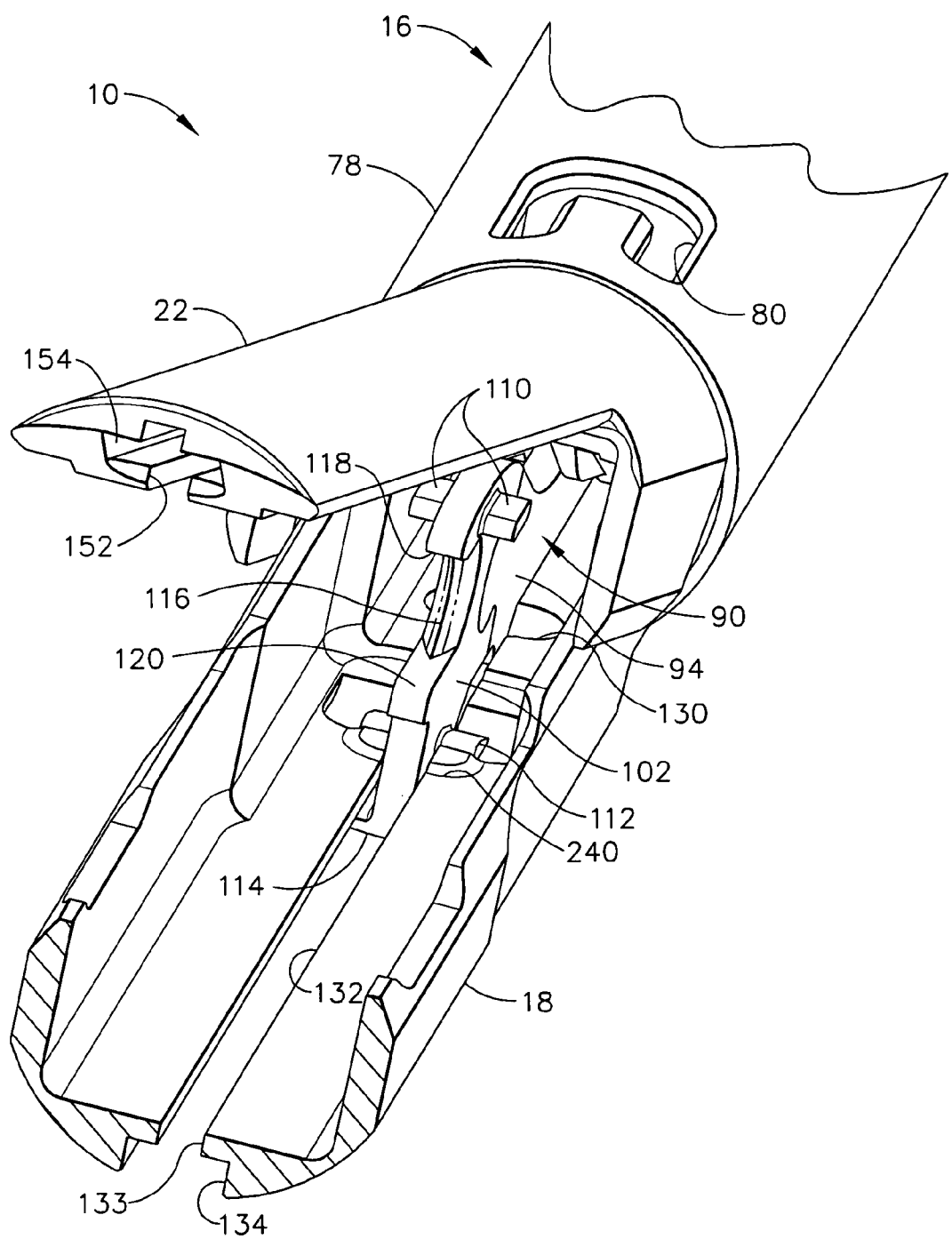
FIG. 7 is a perspective view of the open staple applying assembly of FIG. 2 without the replaceable staple cartridge, a portion of the staple channel proximate to a middle pin of two-piece knife and firing bar, and without a distal portion of a staple channel.

In FIGS. 6–7, the surgical stapling instrument 10 is shown open, with the E-beam 102 filly retracted. During assembly, the lower foot 114 of the E-beam 102 is dropped through a widened hole 130 in the staple channel 18 and the E-beam 102 is then advanced such that the E-beam 102 slides distally along a lower track 132 formed in the staple channel 18. In particular, the lower track 132 includes a narrow slot 133 that opens up as a widened slot 134 on an undersurface of the staple channel 18 to form an inverted T-shape in lateral cross section, as depicted particularly in FIGS. 7 and 8, which communicates with the widened hole 130. Once assembled, the components proximally coupled to the laminate tapered firing bar 94 do not allow the lower foot 114 to proximally travel again to the widened hole 130 to permit disengagement.

In FIG. 9, the laminate tapered firing bar 94 facilitates insertion of the staple applying assembly 12 through a trocar. In particular, a more distal, downward projection 136 raises the E-beam 102 when fully retracted. This is accomplished by placement of the downward projection 136 at a point where it cams upwardly on a proximal edge of the widened hole 130 in the staple channel 18.

In FIG. 10, the laminate tapered firing bar 94 also enhances operation of certain lockout features that may be incorporated into the staple channel 18 by including a more proximal upward projection 138 that is urged downwardly by the shaft frame 70 during an initial portion of the firing travel. In particular, a lateral bar 140 is defined between a pair of square apertures 142 in the shaft frame 70 (FIG. 3). A clip spring 144 that encompasses the lateral bar 140 downwardly urges a portion of the laminate tapered firing bar 94 projecting distally out of the longitudinal firing bar slot 92, which ensures certain advantageous lockout features are engaged when appropriate. This urging is more pronounced or confined solely to that portion of the firing travel when the upward projection 138 contacts the clip spring 144.

In FIGS. 6–7, the E-beam 102 is retracted with the top pins 110 thereof residing within an anvil pocket 150 near the pivoting proximal end of the anvil 22. A downwardly open vertical anvil slot 152 (FIG. 2) laterally widens in the anvil 22 into an anvil internal track 154 that captures the top pins 110 of the E-beam 102 as they distally advance during firing, as depicted in FIGS. 9–10, affirmatively spacing the anvil 22 from the staple channel 18. Thus, with the E-beam 102 retracted, the surgeon is able to repeatably open and close the staple applying assembly 12 until satisfied with the placement and orientation of tissue captured therein for stapling and severing, yet the E-beam 102 assists in proper positioning of tissue even for a staple applying assembly 12 of reduced diameter and correspondingly reduced rigidity.

Figure 8:
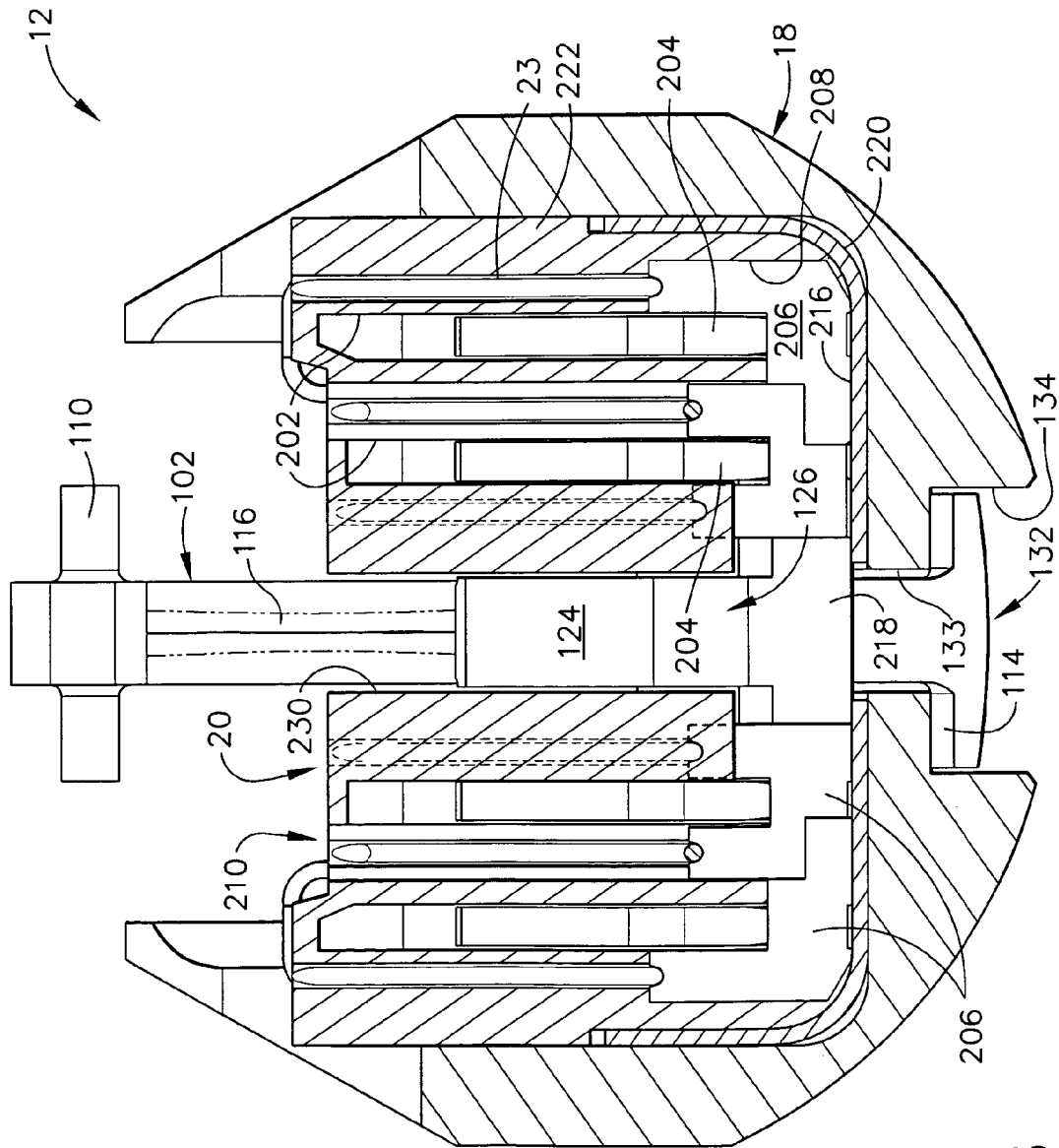
FIG. 8 is a front view in elevation taken in cross section along line 8—8 of the staple applying assembly of FIG. 2 depicting internal staple drivers of the staple cartridge and portions of the two-piece knife and firing bar.

In FIGS. 2–3, 5–6, 8–14, the staple applying assembly 12 is shown with the replaceable staple cartridge 20 that includes the wedge sled 126. Longitudinally aligned and parallel plurality of downwardly open wedge slots 202 (FIG. 8) receive respective wedges 204 integral to the wedge sled 126. In FIGS. 8–10, the wedge sled 126 thus cams upwardly a plurality of staple drivers 206 that are vertically slidable within staple driver recesses 208. In this illustrative version, each staple driver 206 includes two vertical prongs, each translating upwardly into a respective staple hole 210 to upwardly force out and deform a staple 23 resting thereupon against a staple forming surface 214 (FIG. 10) of the anvil 22. A central firing recess 216 (FIG. 3) defined within the staple cartridge 20 proximate to the staple channel 18 allows the passage of the bottom, horizontal portion 218 (FIG. 5) of the wedge sled 126 as well as the middle pins 112 of the E-beam 102. Specifically, a staple cartridge tray 220 (FIGS. 3, 8) attaches to and underlies a polymer staple cartridge body 222 that has the staple driver recesses 208, staple holes 210, and central firing recess 216 formed therein. As staples 23 are thus formed to either side, the sharp cutting edge 116 enters a vertical through slot 230 passing through the longitudinal axis of the staple cartridge 20, excepting only a most distal end thereof.

Firing the staple applying assembly 12 begins as depicted in FIG. 10 with the two-piece knife and firing bar 90 proximally drawn until the downward projection 136 cams the middle guide 120 on the E-beam 102 upward and aft, allowing a new staple cartridge 20 to be inserted into the staple channel 18 when the anvil 22 is open as depicted in FIGS. 2, 6.

Figure 11:
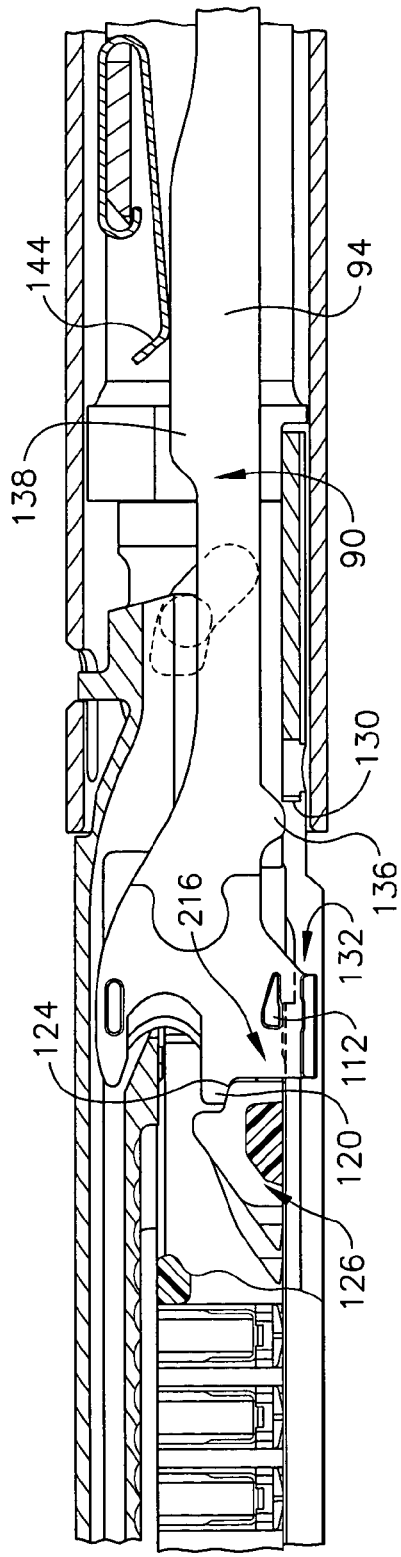
FIG. 11 is a left side detail view in elevation of the staple applying assembly of FIG. 10 with the two-piece knife beginning to fire, corresponding to the configuration depicted in FIG. 9.

In FIG. 11, the two-piece knife and firing bar 90 has been distally advanced a small distance, allowing the downward projection 136 to drop into the widened hole 130 of the lower track 132 under the urging of the clip spring 144 against the upward projection 138 of the laminate tapered firing bar 94. The middle guide 120 prevents further downward rotation by resting upon the stepped central member 124 of the wedge sled 126, thus maintaining the middle pin 112 of the E-beam within the central firing recess 216.

Figure 12:
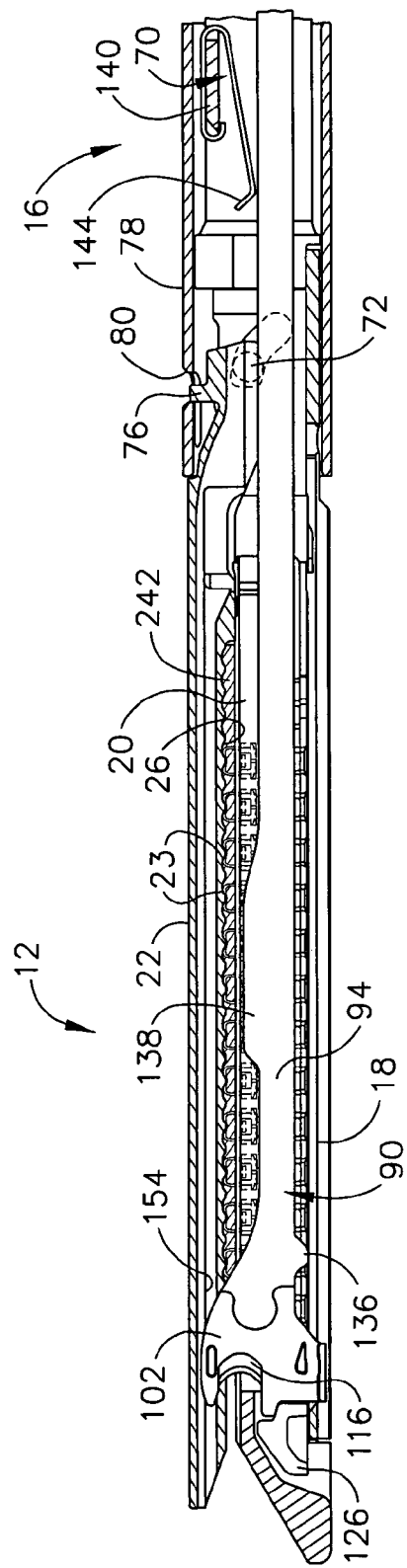
FIG. 12 is a left side cross-sectional view in elevation of the closed staple applying assembly of FIG. 9 after the two-piece knife and firing bar has distally fired.
Figure 13:
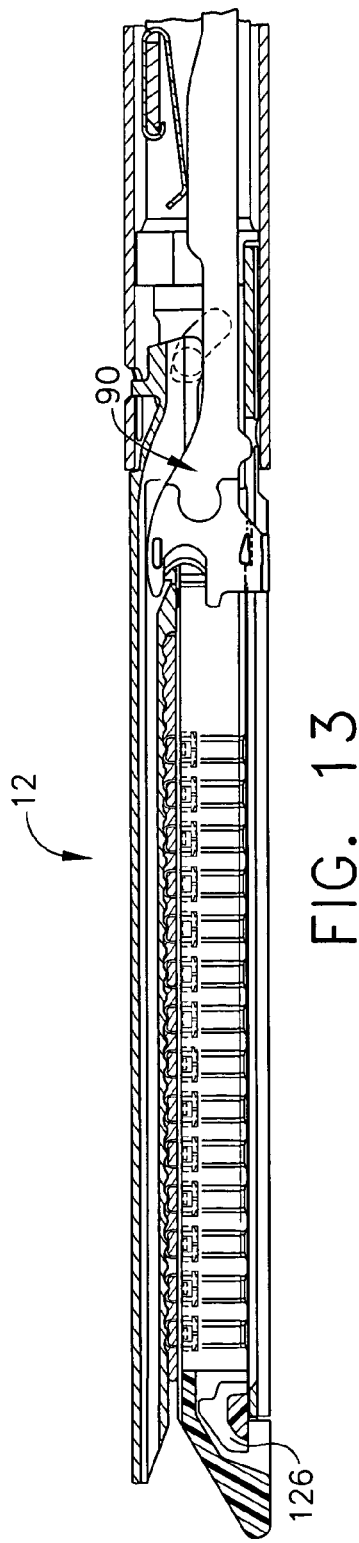
FIG. 13 is a left side cross-sectional view in elevation of the closed staple applying assembly of FIG. 12 after firing of the staple cartridge and retraction of the two-piece knife.

In FIG. 12, the two-piece knife and firing bar 90 has been distally fired, advancing the wedge sled 126 to cause formation of staples 23 while severing tissue 242 clamped between the anvil 22 and staple cartridge 20 with the sharp cutting edge 116. Thereafter, in FIG. 13, the two-piece knife and firing bar 90 is retracted, leaving the wedge sled 126 distally positioned.

Figure 14:
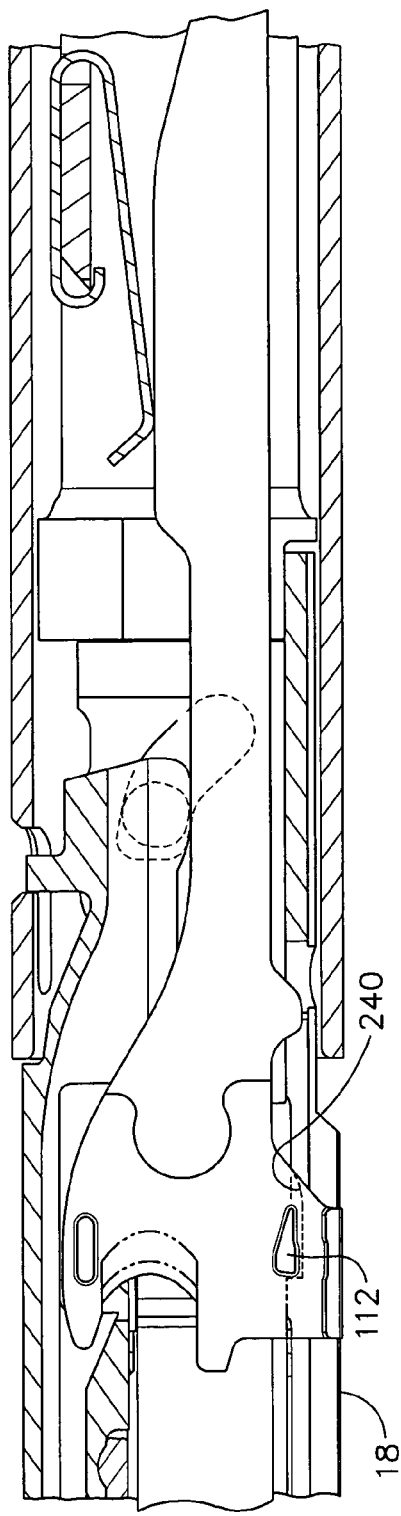
FIG. 14 is a left side cross-sectional detail view in elevation of the staple applying assembly of FIG. 13 with the two-piece knife allowed to drop into a lockout position.
Figure 15:
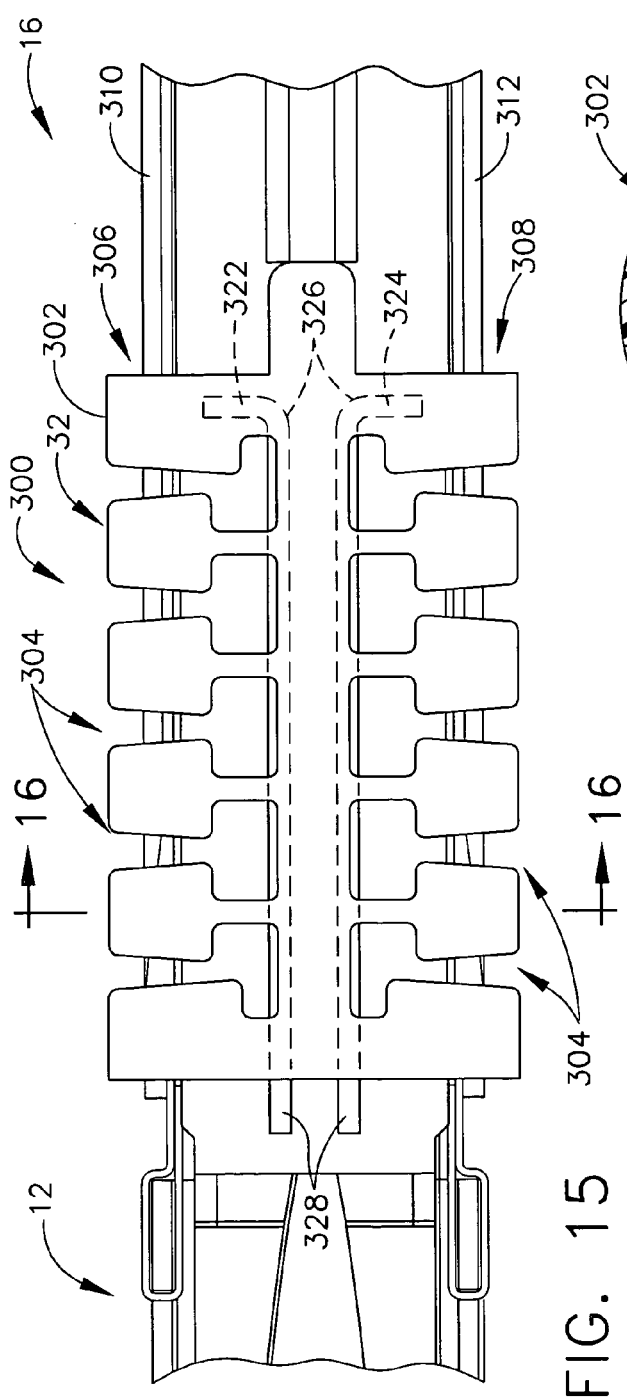
FIG. 15 is a top view in section taken along lines 15—15 of an articulation joint (flex neck) of the surgical stapling instrument of FIG. 1.
Figure 16:
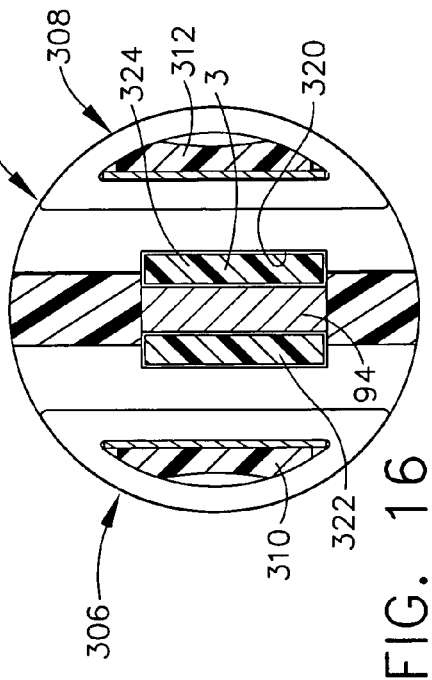
FIG. 16 is a front view in elevation taken in vertical cross section along lines 16—16 of the articulation joint of FIG. 15, showing electroactive polymer (EAP) plate articulation actuators and EAP support plates for a firing bar.
Figure 17:
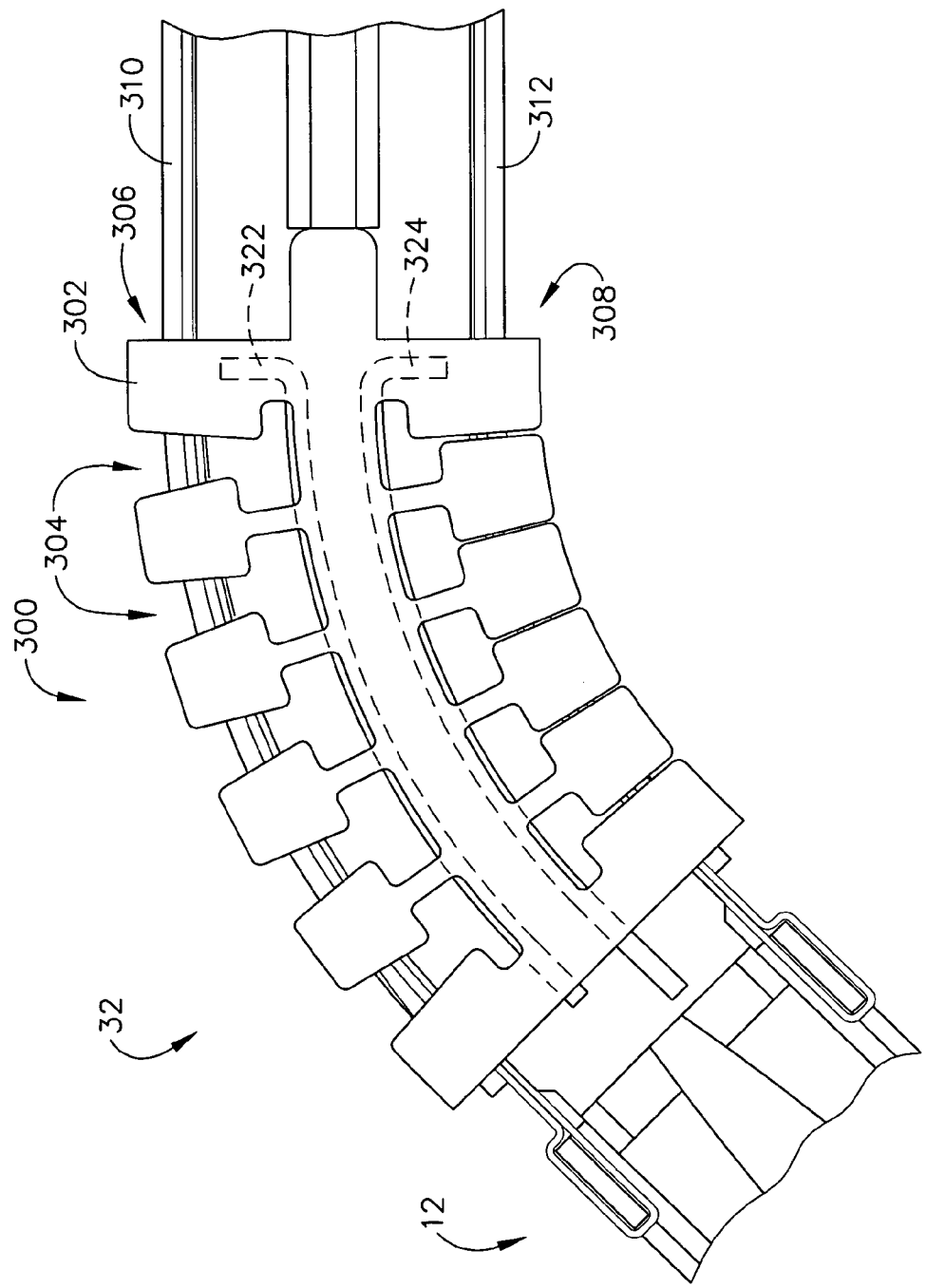
FIG. 17 is a top view in section along lines 15—15 of the articulation joint of FIG. 16 after articulation.
Figure 18:
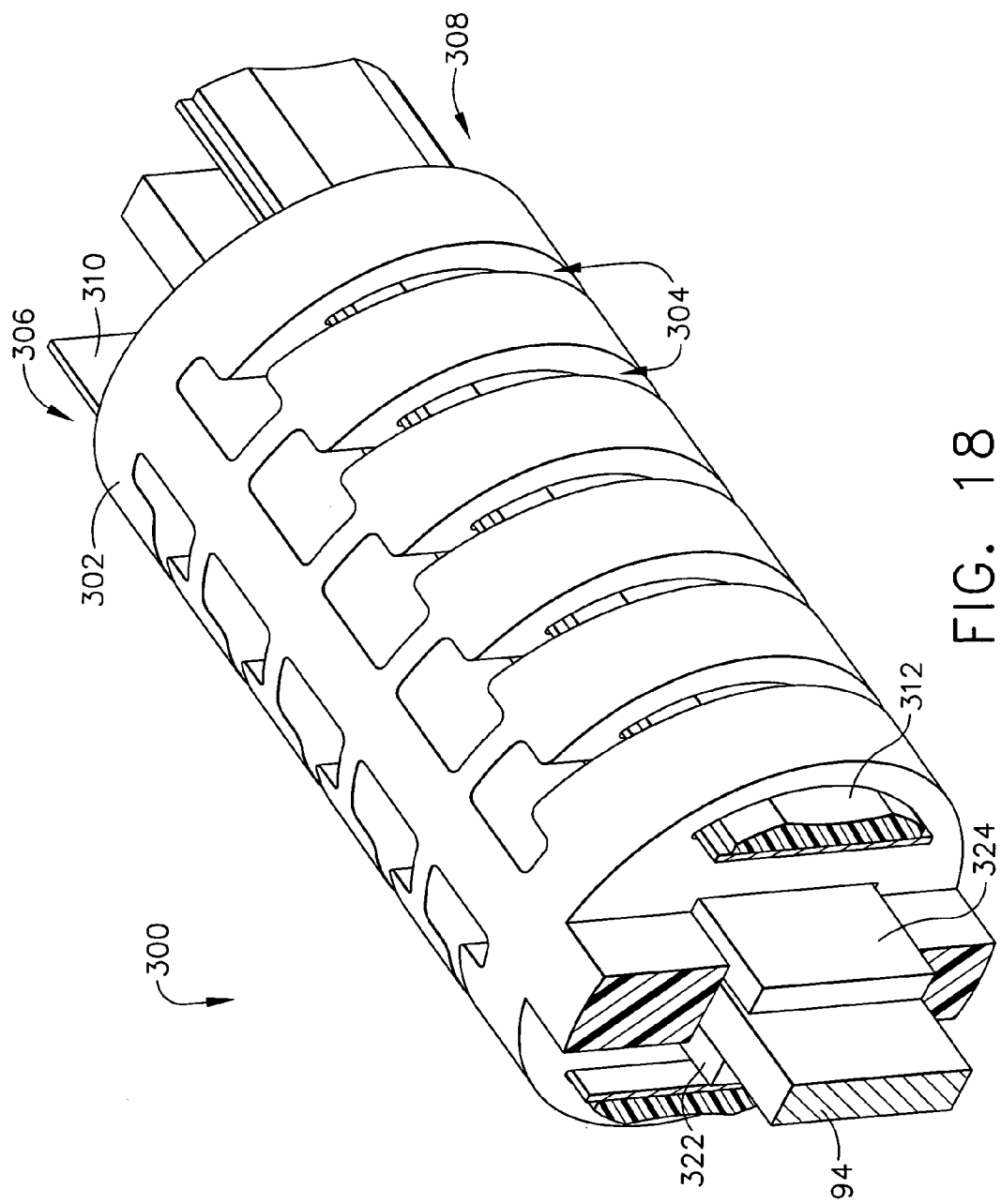
FIG. 18 is a perspective view of the articulation joint of FIG. 15.

In FIG. 14, the middle pin 112 is allowed to translate down into a lockout recess 240 formed in the staple channel 18 (also see FIGS. 7, 10). Thus, the operator would receive a tactile indication as the middle pin 112 encounters the distal edge of the lockout recess 240 when the wedge sled 126 (not shown in FIG. 14) is not proximally positioned (i.e., missing staple cartridge 20 or spent staple cartridge 20).

In FIG. 1, an articulation joint 32 is depicted that advantageously benefits from the flexible strength of the two-piece knife and firing bar 90. In FIGS. 15–18, the articulation joint 32 is depicted as a flex neck joint 300 formed by vertebral column body 302 having laterally symmetric pairs of arcing recesses 304 that allow articulation in an articulation plane. It is generally known to simultaneously compress and expand respective lateral sides 306, 308 by selective movement of control rods (not shown) that longitudinally pass through the respective lateral sides 306, 308. Depicted, however, are EAP plate actuators 310, 312, each capable of powered deflection to one or both lateral directions.

A central passage 320 (FIG. 16) defined longitudinally through the vertebral column body 302 receives a pair of support plates 322, 324 that prevent buckling and binding of the laminate tapered firing bar 94. In the illustrative version, each support plate 322, 324 has a proximal fixed end 326 (FIG. 15) and a sliding end 328 to accommodate changes in radial distance during articulation. Having a firing bar 94 of a thinner thickness is thus supported.

Figure 19:
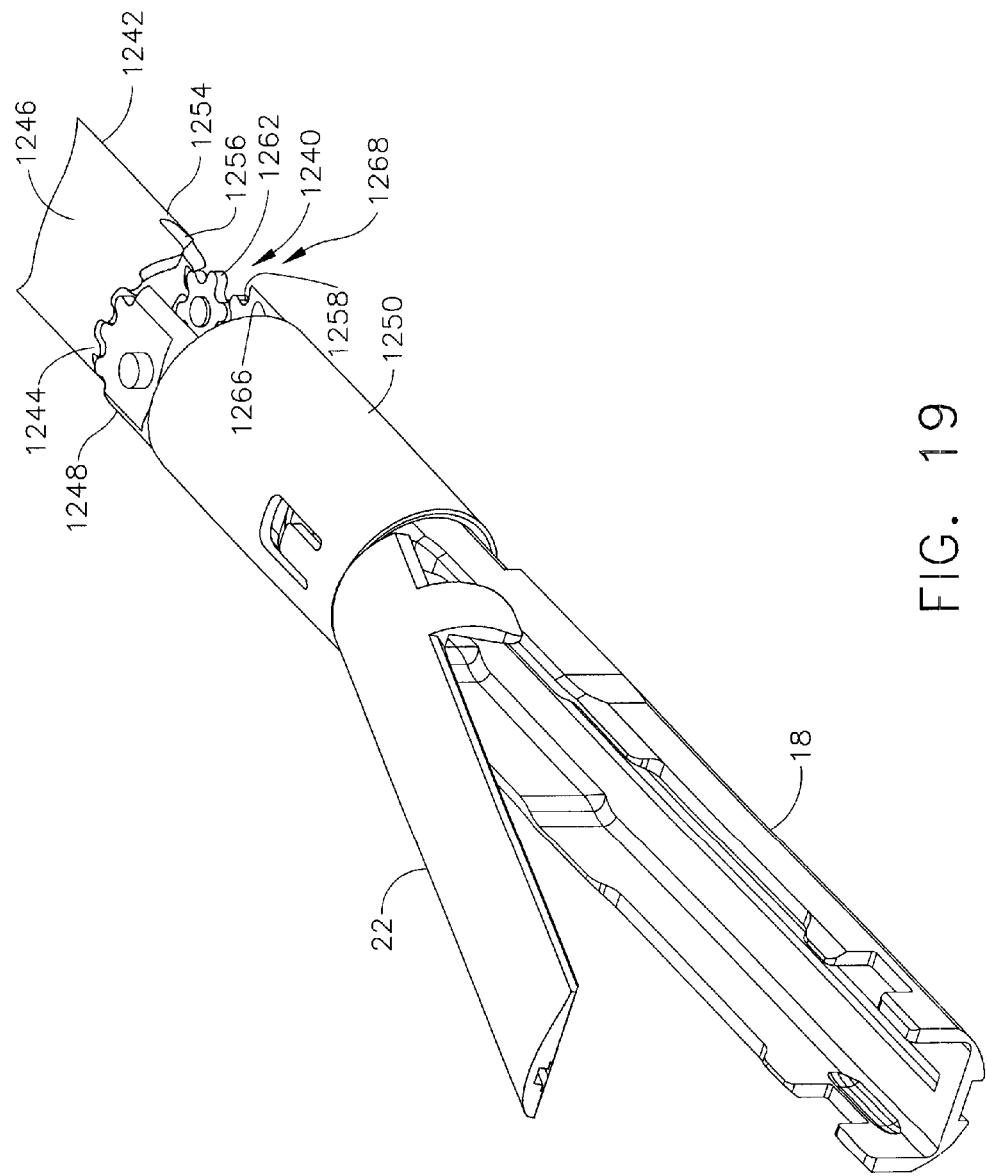
FIG. 19 depicts a top perspective detail view of a spur gear articulation mechanism and end effector for the surgical instrument of FIG. 1 with firing and frame portions removed.
Figure 20:
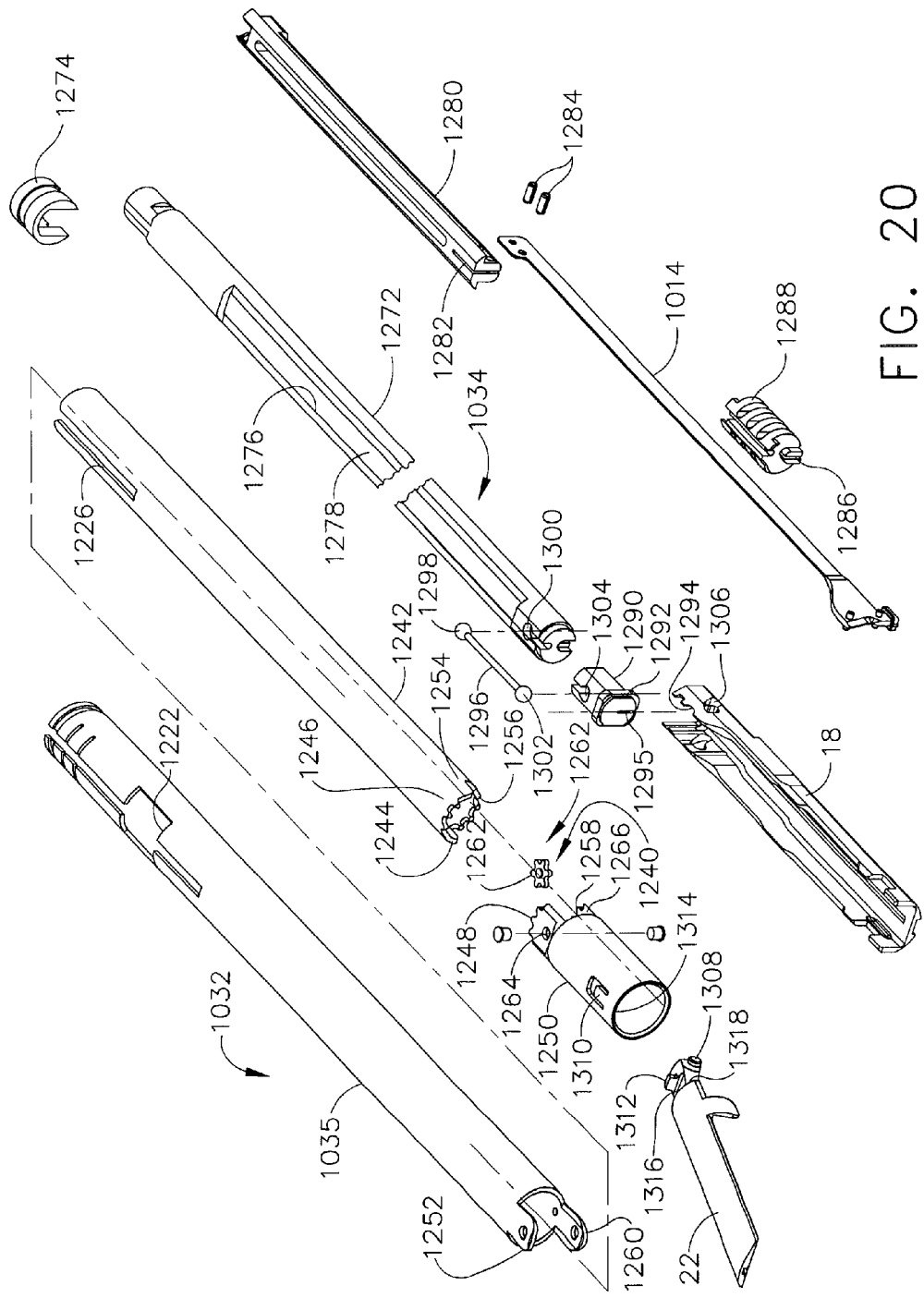
FIG. 20 depicts a perspective, exploded view of the spur gear articulation mechanism of FIG. 19.

FIGS. 19 and 20 depict a spur gear articulation mechanism 240 for the surgical severing and stapling instrument 10 of FIG. 1. Articulation mechanism 1240 has a rotatable hollow articulation drive tube 1242 that is concentrically located within a closure sleeve 1032 and has a distally projecting gear section 1244 about a first circumference portion 1246. Gear section 1244 meshes with a spur gear 1248 attached to and proximally projecting from closure ring 1250 which pivots about pins 1253 extending through first and second pivot points 1252, 1260 projecting distally from the closure sleeve 1032. Thus, an articulation pivot axis passes through both the first and second pivot points 1252, 1260 and pins 1253 rotatably couple closure ring 1250 to the closure sleeve 1032. Rotation of drive 1242 engages the gears 1242 and 1248 and articulates closure ring 1250 about first and second pivot points 1252, 1260.

To increase the effective surface area of gear contact between the hollow articulation drive tube 1242 and the closure ring 1250, a second circumference portion 1254 of the hollow articulation drive tube 1242 has a recessed distally projecting gear section 1256 extending therefrom. Gear section 1256 is operably coupled to a second spur gear 1258 attached to and proximally projecting from an opposite lateral side of the closure ring 1250 by a reversing gear 1262 pivotally supported by frame 1272. Reversing gear 1262 engages both the recessed distally projecting gear section 1256 on one side and the second spur gear 1258 of the closure ring 1250 on the other.

When the closure trigger (not depicted in FIGS. 19–20) is actuated, both the hollow articulation drive tube 1242 and pivotally attached closure tube 1250 of the closure sleeve 1032 are moved distally to close the anvil 18. A closure tube 1035 of the closure sleeve 1032 is spaced away from the closure ring 1250 by pivot points 1252, 1260 pinned to pivot holes 1264 and 1266 centered in spur gears 1248, 1258, and a frame opening 1268 that extends therethrough. The frame opening 1268 provides clearance so that the proximal edges of the closure ring 1250 and the distal edges of the closure tube 1035 of the closure sleeve 1032 do not collide during articulation.

FIG. 11 depicts in disassembled form an implement portion 1270 that includes the spur gear articulation mechanism 1240. The frame 272 is longitudinally attachable to the handle portion (not depicted in FIGS. 19–20) with a bushing 1274 on its proximal end for rotatingly engagement thereto. A frame trough 1276 formed by an opening 1278 longitudinally aligned with the center of the frame 272 is longer than a firing connector 1280 that slides longitudinally within the frame trough 1276. The proximal end of the firing connector 1280 rotatingly engages the distal end of a metal drive bar (not depicted in FIGS. 19–20). The distal end of the firing connector 1280 includes a slot 1282 that receives a proximal end of the firing bar 1014, attached therein by pins 1284. A more distal portion of the firing bar 1014 is positioned within a lower groove 1286 in a firing bar slotted guide 1288 that is distally engaged with an articulating frame member 1290 and the frame 1272.

Articulating frame member 1290 has a channel-anchoring member 1292 that distally attaches to an attachment collar 1294 of a proximal portion in the elongate channel 18. The firing bar 1014 passes through a lower slot 1295 in the articulating frame member 1290. The articulating frame member 1290 is spaced away from the distal end of the frame 1272 by the firing bar slotted guide 1288 and flexibly attached thereto for articulation by a resilient connector 1296. A widened proximal end 1298 of the resilient connector 1296 engages a distally communicating top recess 1300 in the distal end of the frame 1272 and a widened distal end 1302 of the resilient connector 1296 engages a proximally communicating top recess 1304 in the articulating frame member 1290. Thereby, the elongate channel 18 is attached to the handle portion (not shown), albeit with a flexible portion therebetween.

The elongate channel 18 also has an anvil cam slot 1306 that pivotally receives an anvil pivot 1308 of the anvil 22. The closure ring 1250 that encompasses the articulating frame member 1290 includes a distally presented tab 1310 that engages an anvil feature 1312 proximate but distal to the anvil pivot 1308 on the anvil 22 to thereby effect opening. When the closure ring 1250 is moved forward, its distally presented closing face 1314 contacts a ramped cylindrical closing face 1316, which is distal to tab 1312 of the anvil 22. This camming action closes the anvil 22 downward until the closing face 1314 of the closure ring 1250 contacts a flat cylindrical face 1318 of the anvil 22.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while there are a number of advantages to having a wedge sled integral to a staple cartridge, in some applications consistent with aspects of the present invention, the wedge sled may be integral instead to an E-beam. For instance, an entire end effector may be replaceable rather than just the staple cartridge.

What is claimed is:

1. A surgical instrument comprising:
    a handle portion operable to produce a firing motion; and
    an implement portion responsive to the firing motions from the handle portion, the implement portion comprising:
        an elongate channel comprising a distal end and a proximal end and coupled to the handle portion and including a channel slot defining a longitudinal firing axis,
        a staple cartridge received by the elongate channel and incorporating a proximally positioned wedge member aligned to cam upward a driver supporting a staple,
        an anvil pivotally comprising a distal end and a proximal end coupled to the proximal end of the elongate channel and including an anvil channel,
        a firing device including a distally presented cutting edge longitudinally received between the elongate channel and the anvil, an upper member engageable to the anvil channel, a lower member engaging the channel slot, and a middle member operable to actuate the staple cartridge by distally translating the wedge member of the staple cartridge, the firing device positively engaging both the elongate channel and the anvil during movement along the longitudinal firing axis of the firing device to provide spacing therebetween for staple formation,
        an articulation joint proximally coupled to the elongate channel,
        a firing strip proximally attached to the firing device for transferring the firing motion from the handle portion through the articulation joint; and
        an interfacing portion between the firing device and strip formed with a selected one of a group consisting of the firing device and the strip comprising a female recess and the other one of the group comprising a male termination engaged to the female recess for forming an attachment having longitudinal structural strength:
    wherein the firing device is configured to affirmatively space the anvil from the elongate channel during longitudinal travel between the anvil and elongate channel by including a lower portion having an upper surface and a lower surface that slidingly engage the elongate channel;
    wherein the lower member of the firing device comprises a lower pin having the upper surface abutting the elongate channel and the middle member comprises a middle pin having the lower surface opposingly abutting the elongate channel.

2. The surgical instrument of claim 1, wherein the anvil forms a pivotal attachment to the elongate channel inwardly biased at respective distal portions to assist the firing device in affirmatively spacing between the anvil and elongate channel during actuation of the staple cartridge.

3. The surgical instrument of claim 1, wherein the staple cartridge is a selected type of a plurality of staple cartridge types, each staple cartridge type characterized by a thickness selected for a desired spacing between the anvil and elongate channel and characterized by staples having a length suitable for the desired spacing.

4. The surgical instrument of claim 3, wherein the wedge member comprises a wedge sled having a plurality of connected camming wedges each having a preselected height configured for the selected type of staple cartridge, the middle member of the firing device oriented to abut each of the plurality of staple cartridge types.

5. A surgical instrument comprising:
a handle portion operable to produce a firing motion and a closing motion; and
an implement portion responsive to the firing motions from the handle portion and diametrically dimensioned for endo-surgical use, the implement portion comprising:
a shaft coupled to the handle portion operable to separately transfer the firing motion and the closing motion,
an elongate channel coupled to the shaft and including a channel slot defining a longitudinal firing axis,
an anvil pivotally coupled to the elongate channel, responsive to the closing motion from the shaft, and including an anvil channel,
a firing device including a distally presented cutting edge longitudinally received between the elongate channel and the anvil, the firing device including a lower portion slidingly engaged to the elongate channel and an upper portioned positioned to slidingly engage the anvil during firing, engagement of the firing device to the elongate channel and the anvil maintaining a spacing therebetween;
a strip proximally attached to the firing device operable to transfer the firing motion to the firing device; and
an interfacing portion between the firing device and strip formed with a selected one of a group consisting of the firing device and the strip comprising a female recess and the other one of the group comprising a male termination engaged to the female recess for forming an attachment having longitudinal structural strength;
wherein the firing device is configured to affirmatively space the anvil from the elongate channel during longitudinal travel between the anvil and elongate channel by including a lower portion having an upper surface and a lower surface that slidingly engage the elongate channel;
wherein the lower portion of the firing device comprises a lower pin having the upper surface abutting the elongate channel and the lower portion further comprises a middle pin having the lower surface opposingly abutting the elongate channel.

6. The surgical instrument of claim 5, further comprising a staple cartridge engaged by the elongate channel and including a proximally opened slot for receiving the cutting edge of the firing device, the staple cartridge including a plurality of staples cammed upwardly by the movement along the longitudinal firing axis of the firing device.

7. The surgical instrument of claim 6, wherein the staple cartridge further includes a plurality of drivers supporting the plurality of staples and a wedge sled responsive to the distal longitudinal movement of the firing device to cam upwardly the drivers and thus form the plurality of staples against the anvil.

8. The surgical instrument of claim 5, wherein the shaft includes an articulation mechanism through which the strip bends and longitudinally translates.

9. The surgical instrument of claim 6, wherein the staple cartridge is a selected type of a plurality of staple cartridge types, each staple cartridge type characterized by a thickness selected for a desired spacing between the anvil and elongate channel and characterized by staples having a length suitable for the desired spacing.

10. The surgical instrument of claim 9, wherein a selected one of the firing device and the staple cartridge further comprises a plurality of connected camming wedges each having a preselected height configured for the selected type of staple cartridge, the middle member of the firing device oriented to abut each of the plurality of staple cartridge types.

11. The surgical instrument of claim 5, wherein the firing device further comprises an upper member having an upper surface and a lower surface that longitudinally slidingly engage the anvil.

12. The surgical instrument of claim 11, wherein the anvil includes an internal longitudinal slot having a narrowed vertical slot, and wherein the firing device translates in the narrowed vertical slot and includes an upper member having upper and lower surfaces that reside within the internal longitudinal slot for affirmatively spacing the anvil from the elongate channel.

13. The surgical instrument of claim 5, wherein the firing device is configured to affirmatively space the anvil from the elongate channel during longitudinal travel between the anvil and elongate channel by including an upper member having an upper surface and a lower surface that longitudinally slidingly and opposingly engage the anvil.

14. The surgical instrument of claim 13, wherein the anvil includes a longitudinal slot having an upper surface and a lower surface that slidingly abut respectively the lower surface and upper surface of the upper member of the firing device.

15. The surgical instrument of claim 14, wherein the longitudinal slot comprises an internal longitudinal channel communicating with a narrowed vertical slot, and wherein the firing device translates in the narrowed vertical slot and includes an upper member having the upper and lower surfaces that reside within the internal longitudinal channel for affirmatively spacing the anvil from the elongate channel.

16. A surgical instrument comprising:
a handle portion operable to produce a firing motion; and
an implement portion responsive to the firing motions from the handle portion and diametrically dimensioned for endo-surgical use, the implement portion comprising:
a shaft coupled to the handle portion operable to separately transfer the firing motion,
an articulation joint formed in the shaft,
an elongate channel coupled to the shaft,
an anvil pivotally coupled to the elongate channel,
a firing device including a distally presented cutting edge longitudinally received between the elongate channel and the anvil, wherein the firing device comprises a metal forming a rigid cutting implement and the firing device including a lower portion slidingly engaged to the elongate channel and an upper portion positioned to slidingly engage the anvil during firing, engagement of the firing device to the elongate channel and the anvil maintaining a spacing therebetween;

a strip proximally attached to the firing device operable to transfer the firing motion to the firing device and composed of a flexible material for transitioning through the articulation joint; and an interfacing portion between the firing device and strip formed with a selected one of a group consisting of the firing device and the strip comprising a female recess and the other one of the group comprising a male termination engaged to the female recess for forming an attachment having longitudinal structural strength, wherein the firing device is configured to affirmatively space the anvil from the elongate channel during longitudinal travel between the anvil and elongate channel by including an upper member having an upper surface and a lower surface that longitudinally slidingly and opposingly engage the anvil, wherein the anvil includes a longitudinal slot having an upper surface and a lower surface that slidingly abut respectively the lower surface and upper surface of the upper member of the firing device, and wherein the longitudinal slot comprises an internal longitudinal channel communicating with a narrowed vertical slot, and wherein the firing device translates in the narrowed vertical slot and includes an upper member having the upper and lower surfaces that reside within the internal longitudinal channel for affirmatively spacing the anvil from the elongate channel.

\* \* \* \* \*